United States Patent
Garde et al.

(10) Patent No.: US 9,642,976 B2
(45) Date of Patent: May 9, 2017

(54) SYSTEMS AND METHODS FOR INTRA-PULMONARY PERCUSSIVE VENTILATION INTEGRATED IN A VENTILATOR

(71) Applicant: KONINKLIJKE PHILIPS N.V., Eindhoven (NL)

(72) Inventors: Smita Garde, Irvine, CA (US); Samir Ahmad, Irvine, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 185 days.

(21) Appl. No.: 14/356,256

(22) PCT Filed: Nov. 6, 2012

(86) PCT No.: PCT/IB2012/056184
§ 371 (c)(1),
(2) Date: May 5, 2014

(87) PCT Pub. No.: WO2013/068918
PCT Pub. Date: May 16, 2013

(65) Prior Publication Data
US 2015/0027445 A1    Jan. 29, 2015

Related U.S. Application Data

(60) Provisional application No. 61/556,355, filed on Nov. 7, 2011.

(51) Int. Cl.
A61M 16/00 (2006.01)
A61M 16/16 (2006.01)
(Continued)

(52) U.S. Cl.
CPC ........ A61M 16/0069 (2014.02); A61M 16/00 (2013.01); A61M 16/0006 (2014.02);
(Continued)

(58) Field of Classification Search
CPC   A61B 5/087; A61B 5/4848; A61B 2031/001; A61H 2201/1246; A61H 23/00;
(Continued)

(56) References Cited

U.S. PATENT DOCUMENTS 3,955,563 A * 5/1976 Maione ................. A61H 23/04
601/106
6,067,984 A    5/2000 Piper
(Continued)

FOREIGN PATENT DOCUMENTS

WO    0010634 A1    3/2000
WO    2006004439 A2    1/2006
(Continued)

*Primary Examiner* — Annette Dixon

(57) ABSTRACT

System and methods for providing respiratory therapy include predetermined and/or automatically determined perturbations of levels of pressure, flow, and/or other gas parameters integrated and/or combined (Start with a supplied pressurized flow of breathable gas for a subject. The perturbations are intended to improve secretion management through intra-pulmonary percussive ventilation integrated with ventilation therapy.

12 Claims, 4 Drawing Sheets

(51) Int. Cl.
*A61M 16/20* (2006.01)
*A61M 16/06* (2006.01)
*A61B 5/08* (2006.01)
*A61B 5/091* (2006.01)

(52) U.S. Cl.
CPC ........ *A61M 16/0051* (2013.01); *A61M 16/06* (2013.01); *A61M 16/161* (2014.02); *A61M 16/202* (2014.02); *A61M 16/208* (2013.01); *A61B 5/0823* (2013.01); *A61B 5/091* (2013.01); *A61M 16/0066* (2013.01); *A61M 2016/0018* (2013.01); *A61M 2016/0027* (2013.01); *A61M 2016/0036* (2013.01); *A61M 2205/18* (2013.01); *A61M 2205/3303* (2013.01); *A61M 2205/3365* (2013.01); *A61M 2205/3584* (2013.01); *A61M 2205/502* (2013.01); *A61M 2205/505* (2013.01); *A61M 2205/581* (2013.01); *A61M 2205/582* (2013.01); *A61M 2205/583* (2013.01); *A61M 2230/005* (2013.01); *A61M 2230/43* (2013.01); *A61M 2230/46* (2013.01)

(58) Field of Classification Search
CPC ...... A61H 23/04; A61H 31/00; A61H 31/006; A61M 11/06; A61M 16/00; A61M 16/0003; A61M 16/0006; A61M 16/0009; A61M 16/0069; A61M 16/0096; A61M 16/0666; A61M 16/20; A61M 2016/003; A61M 2016/0033; A61M 2205/3317; A61M 2205/3334; A61M 2205/3365; A61M 2205/42; A61M 2205/50; A61M 2205/502; A61M 2205/70; A62B 27/00; A63B 2210/50; B01D 2311/04; B01D 2311/2649; B01D 61/44; B01D 61/50; B01D 61/54; B01D 63/085; B62B 1/045; B62B 2202/404; B62B 2205/123; B62B 5/0033; B62B 5/0066; B62D 51/008; C02F 1/469; C02F 1/4693; C02F 1/4695; C02F 2209/005; C08J 5/20; F16K 11/076; H01M 8/227; Y02E 60/50
USPC ............ 128/200.14, 200.21, 204.18, 204.19, 128/204.21, 204.23, 204.25, 205.24
See application file for complete search history.

(56) References Cited

U.S. PATENT DOCUMENTS

| | | | |
|---|---|---|---|
| 6,581,596 | B1 | 6/2003 | Truitt et al. |
| 6,595,203 | B1 | 7/2003 | Bird |
| 2003/0010344 | A1 | 1/2003 | Bird |
| 2004/0069304 | A1 | 4/2004 | Jam |
| 2010/0125227 | A1 | 5/2010 | Bird |

FOREIGN PATENT DOCUMENTS

| | | |
|---|---|---|
| WO | 2010058308 A2 | 5/2010 |
| WO | 2011058470 A1 | 5/2011 |

\* cited by examiner

SYSTEMS AND METHODS FOR INTRA-PULMONARY PERCUSSIVE VENTILATION INTEGRATED IN A VENTILATOR

CROSS-REFERENCE TO PRIOR APPLICATIONS

This application is the U.S. National Phase application under 35 U.S.C. §371 of International Application No. PCT/IB2012/056184, filed on Nov. 8, 2012, which claims the benefit of U.S. Provisional Patent Application No. 61/556,355, filed on Nov. 7, 2011. These applications are hereby incorporated by reference herein.

BACKGROUND

1. Field

The present disclosure pertains to systems and methods for controlling a ventilation therapy device, and, in particular, for providing and/or operating a respiratory therapy system with integrated intra-pulmonary percussive ventilation.

2. Description of the Related Art

It is well known that subjects who benefit from respiratory therapy, including but not limited to ventilation therapy, may, in certain cases, benefit from assistance with managing secretions. It is known that intrapulmonary percussive ventilation (IPV) may be used to support secretion management and/or secretion mobilization in subjects.

SUMMARY

Accordingly, it is an object of one or more embodiments of the present invention to provide a respiratory therapy system. The system includes a pressure generator configured to generate a pressurized flow of breathable gas for delivery to the airway of a subject, one or more sensors configured to generate one or more output signals conveying information related to one or more gas parameters of the pressurized flow of breathable gas; and one or more processors configured to execute computer program modules. The computer program modules comprise a therapy module configured to determine levels of one or more gas parameters of the pressurized flow of breathable gas as a function of time in accordance with a respiratory therapy regime, a perturbation module configured to determine one or more perturbation parameters defining perturbations to be applied to the levels of the one or more gas parameters determined by the therapy module, a control module configured to control the pressure generator to adjust the one or more gas parameters of the pressurized flow of breathable gas such that the levels of the one or more gas parameters in the pressurized flow of breathable gas are the levels determined by the therapy module with the perturbations defined by the perturbation module, and a breathing parameter determination module configured to determine one or more breathing parameters based on the one or more generated output signals and the perturbation parameters determined by the perturbation module.

It is yet another aspect of one or more embodiments of the present invention to provide a method for providing respiratory therapy. The method comprises generating a pressurized flow of breathable gas for delivery to the artificial airway (tracheal and/or endotracheal tube) or to the natural airway of a subject (collectively referred to herein as "airway"); generating one or more output signals conveying information related to one or more gas parameters of the pressurized flow of breathable gas; determining levels of one or more gas parameters of the pressurized flow of breathable gas as a function of time in accordance with a respiratory therapy regime; determining one or more perturbation parameters defining perturbations to be applied to the determined levels of the one or more gas parameters; determining one or more breathing parameters based on the one or more generated output signals and the determined perturbation parameters; and adjusting the one or more gas parameters of the pressurized flow of breathable gas based on the one or more breathing parameters, such that the levels of the one or more gas parameters of the pressurized flow of breathable gas are the determined levels in accordance with the respiratory therapy regime with the perturbations applied to the determined levels.

It is yet another aspect of one or more embodiments to provide a system for providing respiratory therapy. The system comprises means for generating a pressurized flow of breathable gas for delivery to the airway of a subject; means for generating one or more output signals conveying information related to one or more gas parameters of the pressurized flow of breathable gas; means for determining levels of one or more gas parameters of the pressurized flow of breathable gas as a function of time in accordance with a respiratory therapy regime; means for determining one or more perturbation parameters defining perturbations to be applied to the determined levels of the one or more gas parameters; means for determining one or more breathing parameters based on the one or more generated output signals and the determined perturbation parameters; and means for adjusting the one or more gas parameters of the pressurized flow of breathable gas based on the one or more breathing parameters, such that the levels of the one or more gas parameters of the pressurized flow of breathable gas are the determined levels in accordance with the respiratory therapy regime with the perturbations applied to the determined levels.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
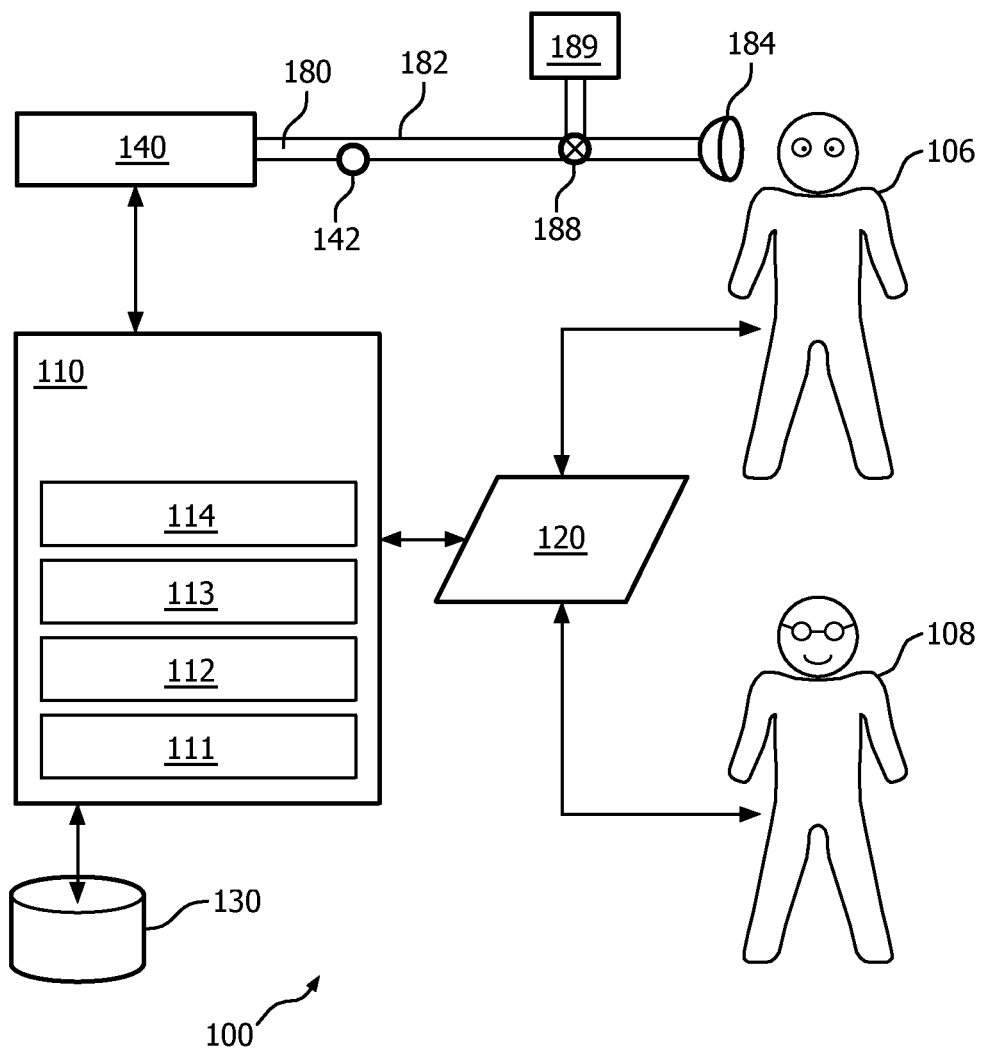
FIG. 1 schematically illustrates a system configured to provide respiratory therapy according to one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a system 100 configured to provide respiratory therapy according to one or more embodiments. System 100 may be implemented as, integrated with, and/or operating in conjunction with a respiratory therapy device. System 100 may support secretion management by delivering some fixed amplitude bursts (compared to common type of respiratory therapy) of a flow of breathable gas at a relatively higher frequency and shorter pulse duration (compared to common breathing rates), which may cause an internal percussion of the lungs of a subject.

System 100 may include one or more of a pressure generator 140, a subject interface 180, an exhalation valve 188, an exhaust circuit 189, one or more sensors 142, an electronic storage 130, a user interface 120, a processor 110, a therapy module 111, a perturbation module 112, a control module 113, a breathing parameter determination module 114, and/or other components.

Pressure generator 140 of system 100 may be integrated, combined, or connected with a ventilator and/or (positive) airway pressure device (PAP/CPAP/BiPAP®/etc.) and configured to provide and/or guide a pressurized flow of breathable gas for delivery to the airway of a subject 106, e.g. via subject interface 180. Subject 106 may or may not initiate one or more phases of respiration. Ventilation therapy may be implemented as pressure control, pressure support, and/or volume control. For example, to support inspiration, the pressure of the pressurized flow of breathable gas may be adjusted to an inspiratory pressure. Alternatively, and/or simultaneously, to support expiration, the pressure and/or flow of the pressurized flow of breathable gas may be adjusted to an expiratory pressure. Other schemes for providing respiratory support through the delivery of the pressurized flow of breathable gas are contemplated, including, but not limited to, assist/control and/or spontaneous ventilation modes, as well as pressure control modes, volume control modes, pressure support modes, and/or other modes. Pressure generator 140 may be configured to adjust pressure levels, flow, volume, humidity, velocity, acceleration, and/or other parameters of the pressurized flow of breathable gas in substantial synchronization with the breathing cycle of the subject.

A pressurized flow of breathable gas may be delivered from and/or via pressure generator 140 to the airway of subject 106 by subject interface 180. Subject interface 180 may include a conduit 182 and/or a subject interface appliance 184. Conduit 182 may be a flexible length of hose, or other conduit, that places subject interface appliance 184 in fluid communication with pressure generator 140. Conduit 182 forms a flow path through which the pressurized flow of breathable gas is communicated between subject interface appliance 184 and pressure generator 140. Subject interface 180 may be in fluid communication with exhalation valve 188, which may in turn be in fluid communication with exhaust circuit 189. Exhaust circuit 189 may include, e.g., an exhaust filter, and/or other components.

Subject interface appliance 184 of system 100 in FIG. 1 may be configured to deliver the pressurized flow of breathable gas to or near the airway of subject 106. As such, subject interface appliance 184 may include any appliance suitable for this function. In one embodiment, pressure generator 140 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of a tracheal and/or an endotracheal tube, a nasal cannula, a tracheotomy tube, a nasal mask, a nasal/oral mask, a full face mask, a total face mask, or other interface appliances that communicate a flow of gas with an airway of a subject. The present disclosure is not limited to these examples, and contemplates delivery of the pressurized flow of breathable gas to subject 106 using any subject interface.

Figure 4A:
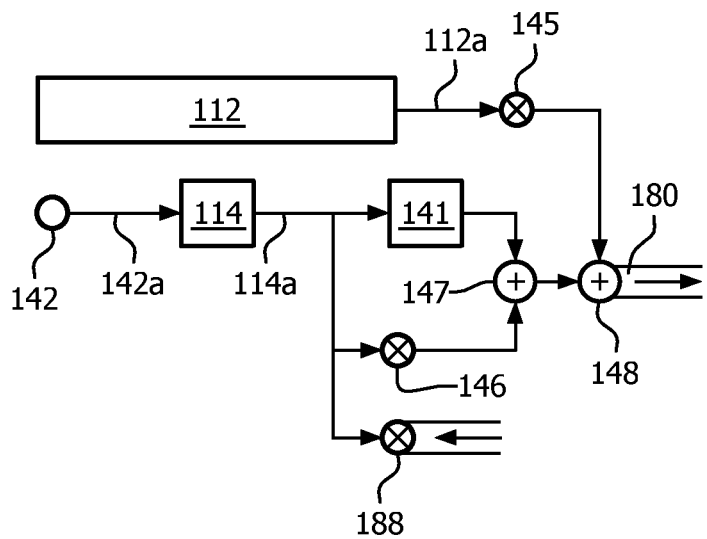
FIGS. 4A-C illustrate various configurations of embodiments of a system configured to provide respiratory therapy.
Figure 4B:
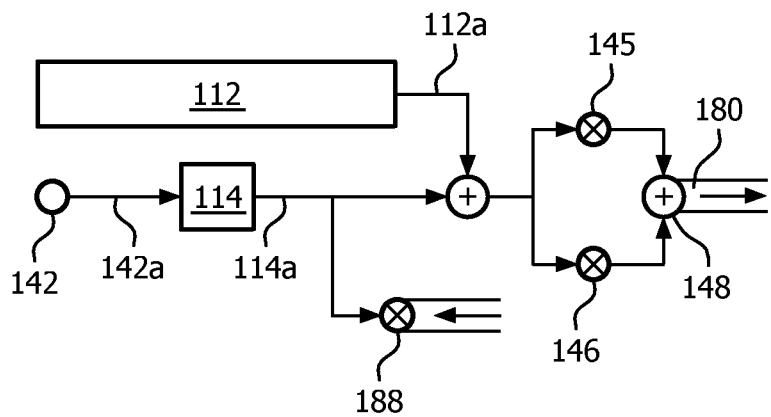

In some embodiments, pressure generator 140 may provide and/or guide the pressurized flow of breathable gas, including but not limited to air, oxygen, heliox (helium-oxygen mixture) and/or oxygen-enriched gas or any combination thereof, via one or more (flow) valves. By way of illustration, FIG. 4B illustrates an exemplary configuration for an embodiment of system 100 in which an air flow valve 145 guides a flow of air and an oxygen flow valve 146 guides a flow of oxygen and/or oxygen-enriched air, such that the combination of both flows, e.g. through a flow merging circuit 148, may be provided to subject interface 180. Control of air flow valve 145 and oxygen flow valve 146 may be based on a combination of a control signal 114a, e.g. derived by breathing parameter determination module 114 from an output signal 142a generated by a sensor 142, and a perturbation control signal 112a, e.g. controlled by perturbation module 112 and derived from one or more perturbation parameters. Control signal 114a may in some embodiments control exhalation valve 188, as depicted in FIG. 4B.

In some embodiments, pressure generator 140 may include a discrete blower 141 to provide a pressurized flow of breathable gas. By way of illustration, FIG. 4A illustrates an exemplary configuration for an embodiment of system 100 in which air flow valve 145 guides a flow of air that is combined, e.g. through a first flow merging circuit 148 (FIG. 4A), with a flow that results from combining the pressurized flow of breathable gas from blower 141 with a flow from oxygen flow valve 146, e.g. through a second flow merging circuit 147 (FIG. 4A). Control of air flow valve 145 may be based on perturbation control signal 112a, e.g. controlled by perturbation module 112 and derived from one or more perturbation parameters. Control of blower 141 and oxygen flow valve 146 may be based on control signal 114a, e.g. derived by breathing parameter determination module 114 from an output signal 142a generated by a sensor 142. Control signal 114a may in some embodiments control exhalation valve 188, as depicted in FIG. 4A.

Figure 4C:
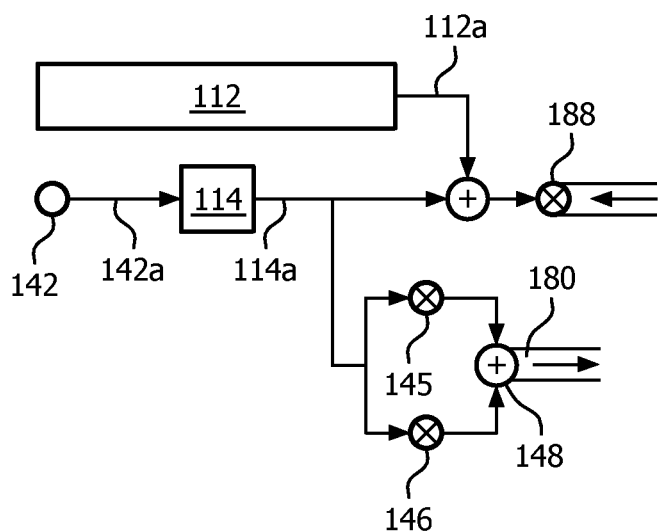

In some embodiments, perturbations in the pressurized flow of breathable gas delivered to the airway of a subject may be controlled through exhalation valve 188. By way of illustration, FIG. 4C illustrates an exemplary configuration for an embodiment of system 100 in which control of exhalation valve 188, and thus control of the flow through exhalation valve 188, may be based on a combination of perturbation control signal 112a, e.g. controlled by perturbation module 112 and derived from one or more perturbation parameters, and control signal 114a, e.g. derived by breathing parameter determination module 114 from an output signal 142a generated by a sensor 142. Control signal 114a may in some embodiments control one or both of air flow valve 145 and/or oxygen flow valve 146. In embodiments that use both, the flows from air flow valve 145 and oxygen flow valve 146 may be combined, e.g. through flow merging circuit 148 (FIG. 4C), and provided to subject interface 180.

Referring to FIG. 1, electronic storage 130 of system 100 comprises electronic storage media that electronically stores information. The electronic storage media of electronic storage 130 may include one or both of system storage that is provided integrally (i.e., substantially non-removable) with system 100 and/or removable storage that is removably connectable to system 100 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 100 to function properly. For example, electronic storage 130 may record or store one or more gas parameters and/or perturbation parameters (as discussed elsewhere herein), information indicating whether the subject adequately complied with a therapy regimen, information indicating whether and/or when a respiratory event occurred, and/or other information. Electronic storage 130 may be a separate component within system 100, or electronic storage 130 may be provided integrally with one or more other components of system 100 (e.g., processor 110).

User interface 120 of system 100 is configured to provide an interface between system 100 and a user (e.g., a user 108, subject 106, a caregiver, a therapy decision-maker, etc.) through which the user can provide information to and receive information from system 100. This enables data, results, and/or instructions and any other communicable items, collectively referred to as "information," to be communicated between the user and system 100. An example of information that may be conveyed to subject 106 is a report detailing the changes in determined breathing parameters throughout a period during which the subject is receiving (respiratory) therapy. An example of information that may be conveyed by the user 108 is the operating mode or ventilation mode of system 100. An example of information that may be conveyed and/or selected by subject 106 and/or user 108 is the perturbation mode of system 100. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 100 from removable storage (e.g., a smart card, a flash drive, a removable disk, etc.) that enables the user(s) to customize the implementation of system 100. Other exemplary input devices and techniques adapted for use with system 100 as user interface 120 include, but are not limited to, an RS-232 port, RF link, an IR link, modem (telephone, cable, Ethernet, internet or other). In short, any technique for communicating information with system 100 is contemplated as user interface 120.

Sensor(s) 142 of system 100 may be configured to generate output signals, e.g. output signal 142a, conveying measurements related to parameters of respiratory airflow or airway mechanics. These parameters may include one or more of flow, (airway) pressure, humidity, velocity, acceleration, and/or other parameters. Sensor 142 may be in fluid communication with conduit 182 and/or subject interface appliance 184. In some embodiments, one or more sensors 142 may be in fluid communication with exhalation valve 188. Generated output signals conveying information pertaining to exhalation valve 188 may be used in various ways, e.g. depending on the ventilation mode, and/or perturbation mode of system 100.

The illustration of sensor 142 including a single member in FIG. 1 is not intended to be limiting. In one embodiment sensor 142 includes a plurality of sensors operating as described above by generating output signals conveying information related to gas parameters of the pressurized flow of breathable gas, and/or parameters associated with the state and/or condition of an airway of subject 106, the breathing of subject 106, the gas breathed by subject 106, and/or the delivery of the gas to the airway of subject 106. For example, a parameter may be related to a mechanical unit of measurement of a component of pressure generator 140 (or of a device that pressure generator 140 is integrated, combined, or connected with) such as flow valve drive current, rotor speed, motor speed, blower speed, fan speed, or a related measurement that may serve as a proxy for any of the previously listed parameters through a previously known and/or calibrated mathematical relationship. Resulting signals or information from sensor 142 may be transmitted to processor 110, user interface 120, electronic storage 130, and/or other components of system 100. This transmission may be wired and/or wireless.

Processor 110 of system 100 is configured to provide information processing capabilities in system 100. As such, processor 110 includes one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some implementations, processor 110 includes a plurality of processing units.

As is shown in FIG. 1, processor 110 is configured to execute one or more computer program modules. The one or more computer program modules include one or more of therapy module 111, perturbation module 112, control module 113, breathing parameter determination module 114, and/or other modules. Processor 110 may be configured to execute modules 111, 112, 113, and/or 114 by software; hardware; firmware; some combination of software, hardware, and/or firmware; and/or other mechanisms for configuring processing capabilities on processor 110.

It should be appreciated that although modules 111, 112, 113, and 114 are illustrated in FIG. 1 as being co-located within a single processing unit, in implementations in which processor 110 includes multiple processing units, one or more of modules 111, 112, 113, and/or 114 may be located remotely from the other modules. The description of the functionality provided by the different modules 111, 112, 113, and/or 114 described below is for illustrative purposes, and is not intended to be limiting, as any of modules 111, 112, 113, and/or 114 may provide more or less functionality than is described. For example, one or more of modules 111, 112, 113, and/or 114 may be eliminated, and some or all of its functionality may be provided by other ones of modules 111, 112, 113, and/or 114. Note that processor 110 may be configured to execute one or more additional modules that may perform some or all of the functionality attributed below to one of modules 111, 112, 113, and/or 114.

Therapy module 111 of system 100 in FIG. 1 is configured to determine levels of one or more gas parameters of the pressurized flow of breathable gas as a function of time in accordance with a respiratory therapy regime. The gas parameters may include one or more of pressure level(s), flow, volume, humidity, velocity, acceleration, gas composition of air, $O_2$, heliox and/or other parameters of the pressurized flow of breathable gas in substantial synchronization with the breathing cycle of the subject, and thus varying over time. The determination by therapy module 111 may be based on one or more of the operating mode, ventilation mode, perturbation mode, breathing mode, and/or other modes of system 100.

Perturbation module 112 of system 100 in FIG. 1 is configured to determine one or more perturbation parameters defining perturbations to be applied to the levels of one or more gas parameters, e.g. the one or more gas parameters determined by therapy module 111. Perturbation parameters may define one or more aspects of perturbations, including, but not limited to, frequency, amplitude, duty cycle, selection of one or more applicable respiratory phases, and/or other aspects of perturbations to be applied to the levels of one or more gas parameters of the pressurized flow of breathable gas. In some embodiments, perturbation module 112 may control perturbation control signal 112a to implement the defined perturbations. One or more perturbation parameters may be automatically adjusted and/or determined based on one or more of the operating mode, ventilation mode, perturbation mode, breathing mode, and/or other modes of system 100. In some embodiments, one or more perturbation parameters may be automatically adjusted and/or determined based on one or more output signals generated by one or more sensors 142. For example, a level of secretion retention, based on one or more outputs signals generated by one or more sensors 142 (or parameters derived therefrom), may form the basis for a determination and/or adjustment of one or more perturbation parameters.

In some embodiments, applying perturbations—by perturbation module 112 in conjunction with other modules of system 100—to the determined levels, by therapy module 111, of one or more gas parameters may be responsive to a determination that a level of secretion retention has breached a threshold level.

Perturbation module 112 may be configured such that one of the perturbation parameters includes a range of frequencies of perturbations to be applied. The range may be, e.g., from 2 Hz to 15 Hz, and/or another range of frequencies. In some modes of operation, perturbation module 112 may gradually, across multiple respiratory cycles, sweep through the range of frequencies. In some modes of operation, perturbation module 112 may randomly determine a frequency within the range of frequencies for one or more respiratory cycles. Other ways to determine a frequency of perturbations within the range of frequencies, including a determination according to one or more predetermined patterns, are contemplated.

Figure 2A:
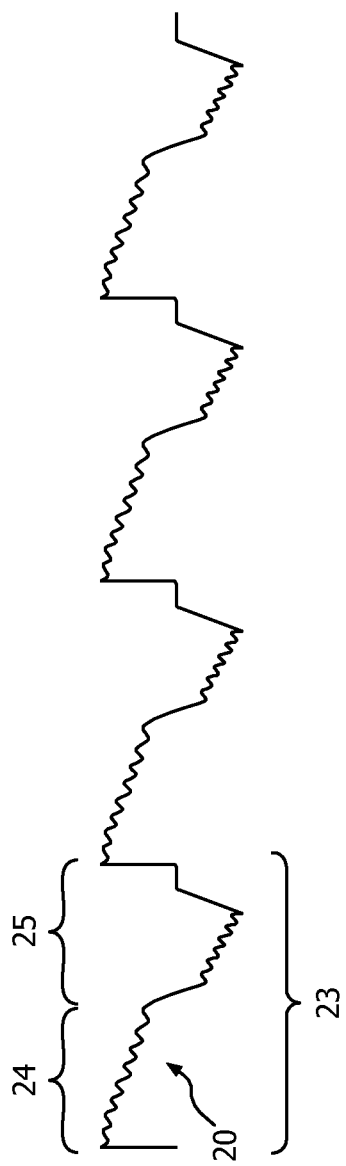
FIGS. 2A-C (i.e., 2A, 2B and 2C) illustrate flow waveforms for one or more embodiments.
Figure 2B:
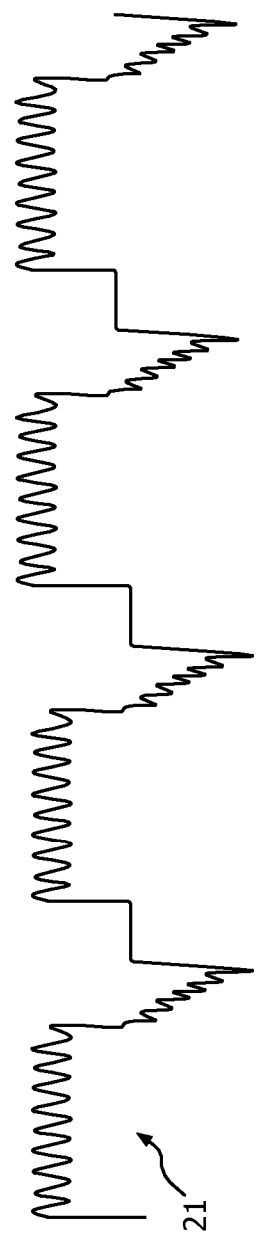
Figure 2C:
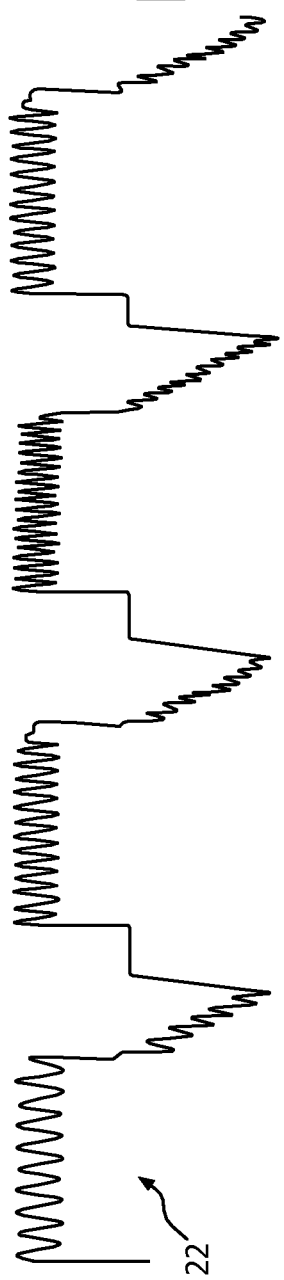

By way of illustration, FIG. 2 illustrates flow waveforms for one or more embodiments. FIG. 2A illustrates a flow waveform 20 in which a first respiratory cycle 23 of four depicted respiratory cycles is divided in an inhalation phase 24 and an exhalation phase 25. Flow waveform 20 may represent a pressure support mode and/or a pressure control mode. The high-frequency perturbations (compared to common breathing rates), depicted in FIG. 2A as approximately eight fluctuations of the flow level during inhalation phase 24 are defined by perturbation parameters that are determined by perturbation module 112. FIG. 2B illustrates a flow waveform 21 which may represent a volume control mode. The high-frequency perturbations of flow waveform 21 in FIG. 2B may have a greater amplitude than the high-frequency perturbations of flow waveform 20 in FIG. 2A. FIG. 2C illustrates a flow waveform 22 which may represent a volume control mode. Four respiratory cycles are depicted in FIG. 2C. The high-frequency perturbations of flow waveform 22 have varying frequencies per respiratory cycle, as may be determined by perturbation module 112.

Referring to FIG. 1, control module 113 of system 100 is configured to control pressure generator 140 to adjust one or more gas parameters of the pressurized flow of breathable gas such that the levels of the one or more adjusted gas parameters are the levels determined by therapy module 111 with the perturbations defined by perturbation module 112 applied.

Breathing parameter determination module 114 of system 100 in FIG. 1 may be configured to determine one or more breathing parameters, gas parameters, and/or other parameters from output signals generated by sensor(s) 142. One or more gas parameters may be related to and/or derived from measurements of one or more of (peak) flow, flow rate, (tidal) volume, pressure, temperature, humidity, velocity, acceleration, gas composition (e.g. concentration(s) of one or more constituents), thermal energy dissipated, (intentional) gas leak, and/or other measurements related to the (pressurized) flow of breathable gas. One or more breathing parameters may be derived from gas parameters and/or other output signals conveying measurements of the pressurized flow of breathable gas. The one or more breathing parameters may include one or more of respiratory rate, breathing period, inhalation time or period, exhalation time or period, respiration flow curve shape, transition time from inhalation to exhalation and/or vice versa, transition time from peak inhalation flow rate to peak exhalation flow rate and/or vice versa, respiration pressure curve shape, maximum proximal pressure drop (per breathing cycle and/or phase), fraction of inspired oxygen, and/or other breathing parameters. Determinations by breathing parameter determination module 114 may be based on the perturbation parameters determined by perturbation module 112. For example, detection of the start of an inhalation or exhalation (sometimes referred to as triggering or cycling) may take perturbations and/or perturbation parameters into account. Respiratory systems using an external and discrete IPV device may not be able to take perturbations and/or perturbation parameters into account for such detections. Breathing parameter determination module 114 may be configured to determine the fraction of inspired oxygen while taking perturbations and/or perturbation parameters into account. Respiratory systems using an external and discrete IPV device may not be able to take perturbations and/or perturbation parameters into account for a determination of the tidal volume in volume control modes. In some embodiments, breathing parameter determination module 114 may use control signal 114a to adjust, e.g. via control module 113, levels of one or more gas parameters of the pressurized flow of breathable gas. Some or all of this functionality may be incorporated or integrated into other computer program modules of processor 110.

Figure 3:
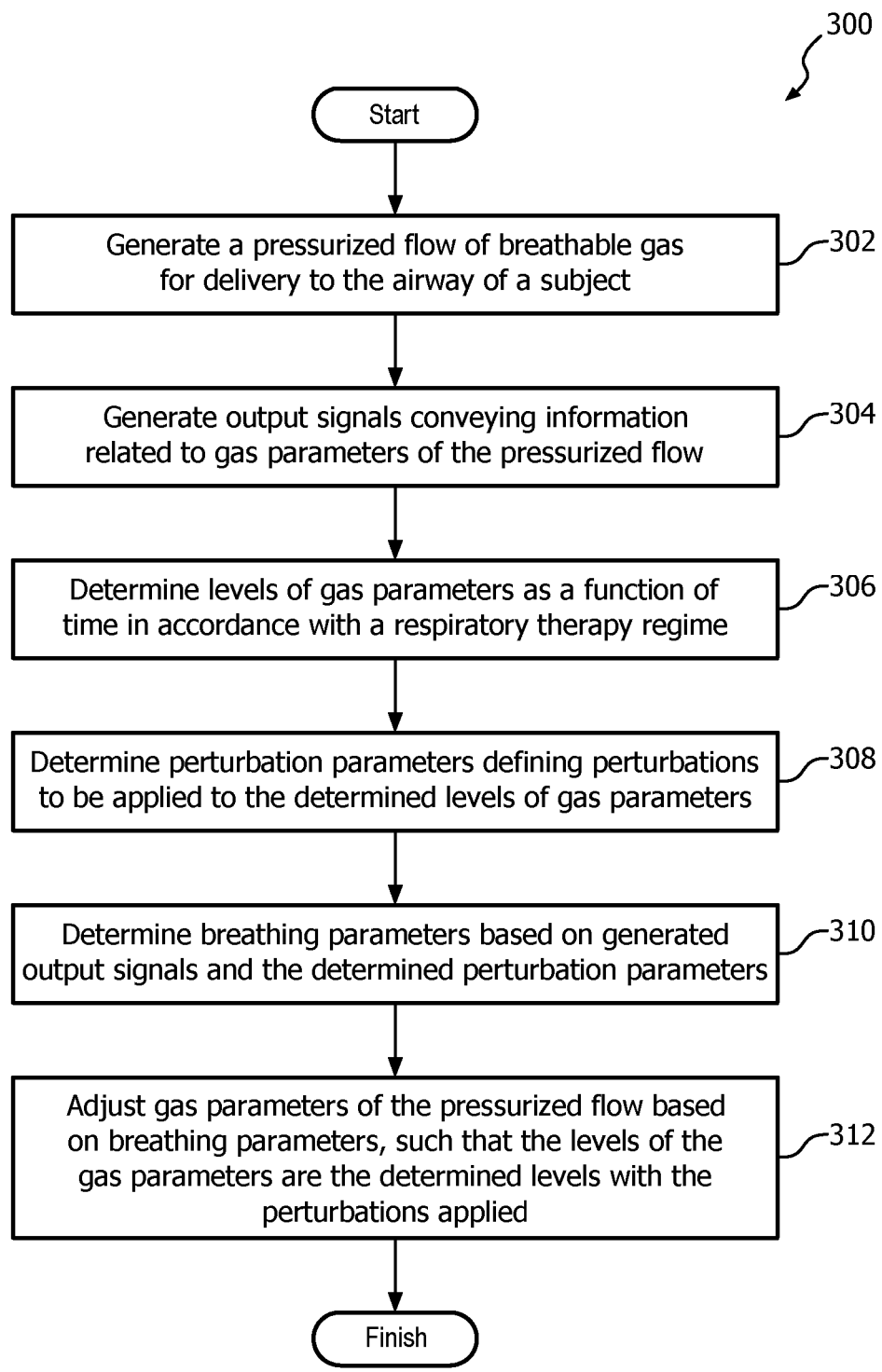
FIG. 3 illustrates a method for providing respiratory therapy according to one or more embodiments.

FIG. 3 illustrates a method 300 for providing respiratory therapy. The operations of method 300 presented below are intended to be illustrative. In some embodiments, method 300 may be accomplished with one or more additional operations not described, and/or without one or more of the operations discussed. Additionally, the order in which the operations of method 300 are illustrated in FIG. 3 and described below is not intended to be limiting. In some embodiments, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, a pressurized flow of breathable gas for delivery to the airway of a subject is generated. In one embodiment, operation 302 is performed by a pressure generator similar to or substantially the same as pressure generator 140 (shown in FIG. 1 and described above).

At an operation 304, one or more output signals are generated that convey information related to gas parameters of the pressurized flow of breathable gas. In one embodiment, operation 304 is performed by a sensor similar to or substantially the same as sensor 142 (shown in FIG. 1 and described above).

At an operation 306, levels of one or more gas parameters are determined as a function of time in accordance with a respiratory therapy regime. In one embodiment, operation 306 is performed by a therapy module similar to or substantially the same as therapy module 111 (shown in FIG. 1 and described above).

At an operation 308, one or more perturbation parameters are determined, wherein perturbation parameters define perturbations to be applied to the determined levels of the one or more gas parameters. In one embodiment, operation 308 is performed by a perturbation module similar to or substantially the same as perturbation module 112 (shown in FIG. 1 and described above).

At an operation 310, one or more breathing parameters are determined based on the one or more output signals and the determined perturbation parameters. In one embodiment, operation 310 is performed by a breathing parameter determination module similar to or substantially the same as breathing parameter determination module 114 (shown in FIG. 1 and described above).

At an operation 312, one or more gas parameters of the pressurized flow of breathable gas are adjusted such that the levels of the gas parameters are the determined levels with the perturbations applied. In one embodiment, operation 312 is performed by a control module similar to or substantially the same as control module 113 (shown in FIG. 1 and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A respiratory therapy system comprising:
   a pressure generator configured to generate a pressurized flow of breathable gas for delivery to the airway of a subject;
   one or more sensors configured to generate one or more output signals conveying information related to one or more gas parameters of the pressurized flow of breathable gas; and
   one or more processors configured to execute computer program modules, the computer program modules comprising:
      a therapy module configured to determine levels of one or more gas parameters of the pressurized flow of breathable gas as a function of time in accordance with a respiratory therapy regime;
      a perturbation module configured (i) to determine one or more perturbation parameters defining perturbations to be applied to the levels of the one or more gas parameters determined by the therapy module and (ii) to output a perturbation parameter control signal, wherein one of the perturbation parameters includes a range of frequencies of perturbations that comprises frequencies higher than a frequency of common breathing rates to be applied as high-frequency fluctuations added to the levels of the one or more gas parameters;

a control module configured to control the pressure generator to adjust the one or more gas parameters of the pressurized flow of breathable gas such that the levels of the one or more gas parameters in the pressurized flow of breathable gas are the levels determined by the therapy module with the perturbations defined by the determined one or more perturbation parameters and applied as high-frequency fluctuations added to the determined levels; and a breathing parameter determination module configured to determine breathing parameters and gas parameters based on (i) the one or more generated output signals of the one or more sensors and (ii) the perturbation parameters determined by the perturbation module, wherein the breathing parameter determination module is further configured to output a breathing parameter control signal in response to the determined breathing parameters and gas parameters, wherein the control module is further configured to adjust, in response to the breathing parameter control signal, the levels of the one or more gas parameters in the pressurized flow of breathable gas, and wherein the perturbation module further determines perturbation parameters defining perturbations selected from the group consisting of: (i) perturbations that gradually, across multiple respiratory cycles, sweep through the range of frequencies, (ii) perturbations having a randomly determined frequency within the range of frequencies for one or more respiratory cycles, and (iii) perturbations having a frequency determined according to one or more predetermined patterns.

2. The respiratory therapy system of claim 1, wherein the breathing parameter determination module is further configured to determine a level of secretion retention from the one or more generated output signals, and wherein the perturbation module is configured to determine the one or more perturbation parameters further based on the determined level of secretion retention.

3. The respiratory therapy system of claim 1, wherein the breathing parameters delineate inhalation phases and exhalation phases, and wherein the determinations of the therapy module and the perturbation module are determined separately for inhalation phases and exhalation phases.

4. The respiratory therapy system of claim 1, wherein the control module is configured to control one or more of a volume of the pressurized flow of breathable gas or a pressure of the pressurized flow of breathable gas to which perturbations are added.

5. A method for providing respiratory therapy, the method comprising:

generating a pressurized flow of breathable gas for delivery to the airway of a subject;

generating one or more output signals conveying information related to one or more gas parameters of the pressurized flow of breathable gas;

determining levels of one or more gas parameters of the pressurized flow of breathable gas as a function of time in accordance with a respiratory therapy regime;

determining one or more perturbation parameters defining perturbations to be applied to the determined levels of the one or more gas parameters, wherein one of the perturbation parameters includes a range of frequencies of perturbations that comprises frequencies higher than a frequency of common breathing rates to be applied as high-frequency fluctuations added to the levels of the one or more gas parameters;

determining one or more breathing parameters and gas parameters based on (a) the one or more generated output signals and (b) the determined perturbation parameters and outputting a breathing parameter control signal in response to the determined breathing parameters and gas parameters; and adjusting the one or more gas parameters of the pressurized flow of breathable gas such that the levels of the one or more gas parameters of the pressurized flow of breathable gas are the determined levels in accordance with the respiratory therapy regime with the perturbations defined by the determined one or more perturbation parameters and applied as high-frequency fluctuations added to the determined levels, and further adjusting, in response to the breathing parameter control signal, the levels of the one or more gas parameters in the pressurized flow of breathable gas, and wherein determining the perturbation parameters further includes defining perturbations selected from the group consisting of: (i) perturbations that gradually, across multiple respiratory cycles, sweep through the range of frequencies, (ii) perturbations having a randomly determined frequency within the range of frequencies for one or more respiratory cycles, and (iii) perturbations having a frequency determined according to one or more predetermined patterns.

6. The method of claim 5, wherein determining the one or more breathing parameters includes determining a level of secretion retention from the one or more generated output signals, and wherein determining the one or more perturbation parameters is further based on the determined level of secretion retention.

7. The method of claim 5, wherein the one or more breathing parameters delineate inhalation phases and exhalation phases, and wherein adjusting the one or more gas parameters of the pressurized flow of breathable gas is performed separately for inhalation phases and exhalation phases.

8. The method of claim 5, wherein the one or more gas parameters of the pressurized flow of breathable gas include one or more of a volume of the pressurized flow of breathable gas or a pressure of the pressurized flow of breathable gas to which perturbations are added.

9. A system for providing respiratory therapy, the system comprising:

means for generating a pressurized flow of breathable gas for delivery to the airway of a subject;

means for generating one or more output signals conveying information related to one or more gas parameters of the pressurized flow of breathable gas;

means for determining levels of one or more gas parameters of the pressurized flow of breathable gas as a function of time in accordance with a respiratory therapy regime;

means for determining one or more perturbation parameters defining perturbations to be applied to the determined levels of the one or more gas parameters and for outputting a perturbation parameter control signal, wherein one of the perturbation parameters includes a range of frequencies of perturbations that comprises frequencies higher than a frequency of common breathing rates to be applied as high-frequency fluctuations added to the levels of the one or more gas parameters;

means for determining breathing parameters and gas parameters based on (i) the one or more generated output signals and (ii) the determined perturbation parameters, wherein the determining means is further for outputting a breathing parameter control signal in response to the determined breathing parameters and gas parameters; and means for adjusting the one or more gas parameters of the pressurized flow of breathable gas such that the levels of the one or more gas parameters of the pressurized flow of breathable gas are the determined levels in accordance with the respiratory therapy regime with the perturbations defined by the determined one or more perturbation parameters and applied as high-frequency fluctuations added to the determined levels, wherein the adjusting means is further configured to adjust, in response to the breathing parameter control signal, the levels of the one or more gas parameters in the pressurized flow of breathable gas, and wherein the perturbation determining means further determines perturbation parameters defining perturbations selected from the group consisting of: (i) perturbations that gradually, across multiple respiratory cycles, sweep through the range of frequencies, (ii) perturbations having a randomly determined frequency within the range of frequencies for one or more respiratory cycles, and (iii) perturbations having a frequency determined according to one or more predetermined patterns.

10. The system of claim 9, wherein the means for determining the one or more breathing parameters further performs a determination of a level of secretion retention from the one or more generated output signals, and wherein operation of the means for determining the one or more perturbation parameters is further based on the determination of the level of secretion retention.

11. The system of claim 9, wherein the one or more breathing parameters delineate inhalation phases and exhalation phases, and wherein operation of the means for adjusting the one or more gas parameters of the pressurized flow of breathable gas is performed separately for inhalation phases and exhalation phases.

12. The system of claim 9, wherein the one or more gas parameters of the pressurized flow of breathable gas include one or more of a volume of the pressurized flow of breathable gas or a pressure of the pressurized flow of breathable gas to which perturbations are added.

* * * * *